United States Patent [19]
Camden

[11] Patent Number: 6,110,953
[45] Date of Patent: *Aug. 29, 2000

[54] PHARMACEUTICAL COMPOSITION FOR INHIBITING THE GROWTH OF CANCERS

[75] Inventor: James Berger Camden, West Chester, Ohio

[73] Assignee: The Procter & Gamble Company, Cincinnati, Ohio

[*] Notice: This patent is subject to a terminal disclaimer.

[21] Appl. No.: 09/245,520

[22] Filed: Feb. 5, 1999

Related U.S. Application Data

[62] Division of application No. 08/674,182, Jul. 16, 1996.

[51] Int. Cl.⁷ .................................................. A61K 31/425

[52] U.S. Cl. .......................................... 514/383; 514/310

[58] Field of Search ...................................... 514/383, 310

[56] References Cited

U.S. PATENT DOCUMENTS

| | | | |
|---|---|---|---|
| 4,079,062 | 3/1978 | Van Reet et al. | 548/268.8 |
| 4,160,838 | 7/1979 | Van Reet et al. | 424/269 |
| 4,490,540 | 12/1984 | Heeres | 548/336 |
| 5,114,951 | 5/1992 | King | 514/290 |
| 5,211,736 | 5/1993 | Lai | 504/275 |

*Primary Examiner*—James O. Wilson
*Assistant Examiner*—Howard Owens
*Attorney, Agent, or Firm*—Rose Ann Dabek; Jacobus C. Rasser

[57] ABSTRACT

A pharmaceutical composition that inhibits the growth of tumors and cancers in mammals that comprises a 1H-1,2,4-triazole derivative along with a safe and effective amount of a chemotherapeutic agent. Potentiators can be used to enhance the effectiveness of the drugs. The triazoles and potentiators compounds can also be used to treat viral infections.

23 Claims, No Drawings

PHARMACEUTICAL COMPOSITION FOR INHIBITING THE GROWTH OF CANCERS

This is a division of application Ser. No. 08/674,182, filed on Jul. 16, 1996.

TECHNICAL FIELD

This invention is a pharmaceutical composition that inhibits the growth of cancers, leukemia and tumors in mammals, particularly in human and warm blooded animals. The composition contains a 1H-1,2,4-triazole derivative and a chemotherapeutic agent.

BACKGROUND OF THE INVENTION

Cancers are the leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but not all types of cancers and tumors respond to these agents. Unfortunately, many of these agents also destroy normal cells. The exact mechanism for the action of these chemotherapeutic agents are not always known.

Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and anti-metabolites form the bulk of therapies available to oncologists. Ideally cytotoxic agents that have specificity for cancer and tumor cells while not affecting normal cells would be extremely desirable. Unfortunately, none have been found and instead agents which target especially rapidly dividing cells (both tumor and normal) have been used.

Clearly, the development of materials that would target tumor cells due to some unique specificity for them would be a breakthrough. Alternatively, materials that were cytotoxic to tumor cells while exerting mild effects on normal cells would be desirable. It is believed that the 1H-1,2,4-triazole when used in conjunction with chemotherapeutic agents can both reduce and suppress the growth of cancers, tumors and leukemia. Therefore, it is an object of this invention to provide a pharmaceutical composition that is effective in suppressing and inhibiting the growth of tumors and cancers in mammals with mild or no effects on normal cells.

It has been found that the 1H-1,2,4-triazole derivatives are especially effective in suppressing the growth of the cancer, tumor, virus, or bacteria. The use of these 1H-1,2,4-triazole derivative in combination with other chemotherapeutic agents which are effective in destroying the tumor is a novel method of treatment of cancers and tumors More specifically, it is an object of this invention to provide an anti-cancer composition comprising a pharmaceutical carrier and a 1H-1,2,4-triazole derivative and a chemotherapeutic agent along with a method for treating such cancers. Potentiators may also enhance the effectiveness of this composition.

These and other objects will become evident from the following detailed description of this inventions.

SUMMARY OF THE INVENTION

A pharmaceutical composition for treatment of mammals, and in particular, warm blooded animals and humans, comprising a pharmaceutical carrier and an effective amount of a chemotherapeutic agent and a safe effective amount of an anti-cancer compound selected from the group consisting of:

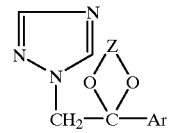

wherein Z is an alkylene selected from the group consisting of $CH_2$—$CH_2$—, —$CH_2$—$CH_2$—$CH_2$—, —$CH(CH_3)$—$CH(CH_3)$— and —$CH_2$—$CH$(alkyl) wherein said alkyl has from 1 to about 10 carbon atoms; and Ar is a member selected from the group consisting of phenyl, substituted phenyl, thienyl, halothienyl, naphthyl and fluorenyl, wherein "substituted phenyl" has the meaning of a phenyl radical having thereon from 1 to 3 substituents selected independently from the group consisting of halo, lower alkyl, lower alkyloxy, cyano and nitro. The therapeutically active acid addition salts of the foregoing compound (I) are also embraced within the scope of this invention.

As used in the foregoing definition of Z, the term "alkyl" is meant to include straight and branch chained hydrocarbon radicals having from 1 to about 10 carbon atoms, such as, for example, methyl, ethyl, 1-methylethyl, propyl, 1,1-dimethylethyl, butyl, pentyl, hexyl, heptyl, octyl, decyl and the like; as used herein "lower alkyl" may be straight or branch chained saturated hydrocarbons having from 1 to 6 carbon atoms, such as, for example, methyl, ethyl, propyl, 1-methylethyl, butyl, 1,1-dimethylethyl, pentyl, hexyl and the like alkyls; and the term "halo" is generic to halogen atoms of atomic weight less than 127; i.e., fluoro, chloro, bromo and iodo.

These compositions can be used to inhibit the growth of cancers and other tumors in humans or animals by administration of an effective amount either orally, rectally, topically or parenterally, intravenously or by injection into the tumor. These compositions do not significantly affect healthy cells as compared to adriamycin which has a detrimental effect on healthy cells. Potentiators may be included in the compositions.

The 1H-1,2,4-triazole derivatives along with the potentiators compositions can also be used to treat viruses. Combinations with other fungicides are also effective.

DETAILED DESCRIPTION OF THE INVENTION

A. Definitions:

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical addition salts" is salt of the anti-cancer compound with an organic or inorganic acid. These preferred acid addition salts are chlorides, bromides, sulfates, nitrates, phosphates, sulfonates, formates, tartrates, maleates, malates, citrates, benzoates, salicylates, ascorbates, and the like.

As used herein, a "pharmaceutical carrier" is a pharmaceutically acceptable solvent, suspending agent or vehicle for delivering the anti-cancer agent to the animal or human. The carrier may be liquid or solid or liposomes and is selected with the planned manner of administration in mind.

As used herein, "cancer" refers to all types of cancers or neoplasm or malignant tumors and all types of cancers including leukemia that are found in mammals.

As used herein, the "anti-cancer compounds" are the 1H-1,2,4-triazoles and their salts. The exact 1H-1,2,4-triazoles are described in detail below. The preferred materials are the products sold under the names "propiconazole®" by Janssen Pharmaceutical NV (Belgium).

As used herein, "viruses" includes viruses which cause diseases (viral infections) in man and other warm blooded animals, such as HIV virus, herpes, influenza and rhinoviruses.

As used herein "chemotherapeutic agents" includes DNA-interactive Agents, Antimetabolites, Tubulin-Interactive Agents, Hormonal agents and others, such as Asparaginase or hydroxyurea.

As used herein "potentiators" are materials such as tripolidine and its cis-isomer and procodazole which are used in combination with the chemotherapeutic agents and the 1H-1,2,4-triazole derivative.

B. The Anti-Cancer Compounds

The anti-cancer compounds are 1H-1,2,4-triazole derivatives which are known for their antifungal activities. They are systemic materials used to prevent and eradicate fungi. The compounds have the following structure:

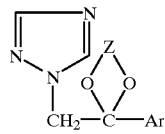

wherein Z is an alkylene selected from the group consisting of $CH_2$—$CH_2$—, —$CH_2$—$CH_2$—$CH_2$—, —$CH(CH_3)$—$CH(CH_3)$— and —$CH_2$—$CH(alkyl)$ wherein said alkyl has from 1 to about 10 carbon atoms; and Ar is a member selected from the group consisting of phenyl, substituted phenyl, thienyl, halothienyl, naphthyl and fluorenyl, wherein "substituted phenyl" has the meaning of a phenyl radical having thereon from 1 to 3 substituents selected independently from the group consisting of halo, lower alkyl, lower alkyloxy, cyano and nitro. The therapeutically active acid addition salts of the foregoing compound (I) are also embraced within the scope of this invention.

As used in the foregoing definition of Z, the term "alkyl" is meant to include straight and branch chained hydrocarbon radicals having from 1 to about 10 carbon atoms, such as, for example, methyl, ethyl, 1-methylethyl, propyl, 1-dimethylethyl, butyl, pentyl, hexyl, heptyl, octyl, decyl and the like; as used herein "lower alkyl" may be straight or branch chained saturated hydrocarbons having from 1 to 6 carbon atoms, such as, for example, methyl, ethyl, propyl, 1-methylethyl, butyl, 1,1-dimethylethyl, pentyl, hexyl and the like alkyls; and the term "halo" is generic to halogen atoms of atomic weight less than 127; i.e., fluoro, chloro, bromo and iodo. Their pharmaceutically acceptable acid addition salts with both organic and inorganic acids can also be used herein.

Preferred derivatives include:
1[-[2-(2,4-dichlorophenyl)-1,3-dioxolan-2-yl]methyl]-1H-1,2,4-triazole,
1-[2-(2,4-dichlorophenyl)-4-methyl-1,3-dioxolan-2-ylmethyl]-1H-1,2,4-triazole,
1-[2-(2,4-dichlorophenyl)-4-ethyl-1,3-dioxolan-2-ylmethyl]-1H-1,2,4-triazole,
1-[2-(2,4-dichlorophenyl)-4-propyl-1,3-dioxolan-2-ylmethyl]-H-1,2,4-triazole,
1-[2-(2,4-dichlorophenyl)-4-pentyl-1,3-dioxolan-2-ylmethyl]-1H-1,2,4-triazole, and the therapeutically active acid addition salts thereof.

These compounds are prepared according to the method described in U.S. Pat. No. 4,079,062 issued to Van Reet, et al, Mar 14, 1978.

It is believed that these particular materials in combination with chemotherapeutic agents and optionally potentiators, have the capability of reducing tumors or decreasing their growth significantly because of their ability to inhibit the synthesis of sterols.

C. Chemotherapeutic Agents

The chemotherapeutic agents are generally grouped as DNA-interactive Agents, Antimetabolites, Tubulin-Interactive Agents, Hormonal agents and others such as Asparaginase or hydroxyurea. Each of the groups of chemotherapeutic agents can be further divided by type of activity or compound. The chemotherapeutic agents used in combination with the 1H-1,2,4-triazole derivative of this invention include members of all of these groups. For a detailed discussion of the chemotherapeutic agents and their method of administration, see Dorr, et al, *Cancer Chemotherapy Handbook,* 2d edition, pages 15–34, Appleton & Lange (Connecticut, 1994) herein incorporated by reference.

DNA-Interactive Agents include the alkylating agents, e.g. Cisplatin, Cyclophosphamide, Altretamine; the DNA strand-breakage agents, such as Bleomycin; the intercalating topoisomerase II inhibitors, e.g., Dactinomycin and Doxorubicin); the nonintercalating topoisomerase II inhibitors such as, Etoposide and Teniposide; and the DNA minor groove binder Plicamycin.

The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. Typical alkylating agents include:

Nitrogen mustards, such as Chlorambucil, Cyclophosphamide, Isofamide, Mechlorethamine, Melphalan, Uracil mustard;

Aziridine such as Thiotepa methanesulphonate esters such as Busulfan;

nitroso ureas, such as Carmustine, Lomustine, Streptozocin;

platinum complexes, such as Cisplatin, Carboplatin;

bioreductive alkylator, such as Mitomycin, and Procarbazine, Dacarbazine and Altretamine;

DNA strand breaking agents include Bleomycin;

DNA topoisomerase II inhibitors include the following:

Intercalators, such as Amsacrine, Dactinomycin, Daunorubicin, Doxorubicin, Idarubicin, and Mitoxantrone;

nonintercalators, such as Etoposide and Teniposide.

The DNA minor groove binder is Plicamycin.

The antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The antimetabolites useful herein include:

folate antagonists such as Methotrexate and trimetrexate pyrimidine antagonists, such as Fluorouracil, Fluorodeoxyuridine, CB3717, Azacitidine, Cytarabine, and Floxuridine purine antagonists include Mercaptopurine, 6-Thioguanine, Fludarabine, Pentostatin;

sugar modified analogs include Cyctrabine, Fludarabine;

ribonucleotide reductase inhibitors include hydroxyurea.

Tubulin Interactive agents act by binding to specific sites on tubulin, a protein that polymerizes to form cellular microtubules. Microtubules are critical cell structure units. When the interactive agents bind on the protein, the cell can not form microtubules Tubulin Interactive agents include Vincristine and Vinblastine, both alkaloids and Paclitaxel.

Hormonal agents are also useful in the treatment of cancers and tumors. They are used in hormonally susceptible tumors and are usually derived from natural sources. These include:

estrogens, conjugated estrogens and Ethinyl Estradiol and Diethylstilbesterol, Chlortrianisen and Idenestrol;

progestins such as Hydroxyprogesterone caproate, Medroxyprogesterone, and Megestrol;

androgens such as testosterone, testosterone propionate; fluoxymesterone, methyltestosterone;

Adrenal corticosteroids are derived from natural adrenal cortisol or hydrocortisone. They are used because of their anti inflammatory benefits as well as the ability of some to inhibit mitotic divisions and to halt DNA synthesis. These compounds include, Prednisone, Dexamethasone, Methylprednisolone, and Prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include:

antiestrogenic agents such as Tamosifen, antiandrogen agents such as Flutamide; and antiadrenal agents such as Mitotane and Aminoglutethimide.

Hydroxyurea appears to act primarily through inhibition of the enzyme ribonucleotide reductase.

Asparagenase is an enzyme which converts asparagine to nonfunctional aspartic acid and thus blocks protein synthesis in the tumor.

D. Potentiators

The "potentiators" can be any material which improves or increase the efficacy of the pharmaceutical composition. They include immunosuppressors or materials which act on the immune system. One such potentiator is triprolidine and its cis-isomer which are used in combination with the chemotherapeutic agents and the 1H-1,2,4-triazole derivative. Triprolidine is described in U.S. Pat. No. 5,114,951 (1992).

Another potentiator is procodazole, 1H-Benzimidazole-2-propanoic acid; [β-(2-benzimidazole) propionic acid; 2-(2-carboxyethyl)benzimidazole; propazol]. Procodazole is a non-specific active immunoprotective agent against viral and bacterial infections and can be used with the compositions claimed herein. It is effective with the 1H-1,2,4-triazoles alone in treating cancers, tumors, leukemia and viral infections or with chemotherapeutic agents.

Propionic acid and its salts and esters can also be used in combination with the pharmaceutical compositions claimed herein.

Antioxidant vitamins such as vitamins A, C and E and beta-carotene can be added to these compositions.

E. Dosage

Any suitable dosage may be given in the method of the invention. The type of disease (cancer, leukemia or virus), the compound, the carrier and the amount will vary widely depending on the species of the warm blooded animal or human, body weight, and tumor being treated. Generally a dosage of between about 2 milligrams (mg) per kilogram (kg) of body weight and about 400 mg per kg of body weight is suitable. Preferably from 15 mg to about 150 mg/kg of body weight is used. For the chemotherapeutic agents a lower dosage may be appropriate, e.g. 0.5 mg/kg body weight to 400 mg/kg body weight. Generally, the dosage in man is lower than for small warm blooded mammals such as mice. A dosage unit may comprise a single compound or mixtures thereof with other compounds or other cancer inhibiting compounds. The dosage unit can also comprise diluents, extenders, carriers and the like. The unit may be in solid or gel form such as pills, tablets, capsules and the like or in liquid form suitable for oral, rectal, topical, intravenous injection or parenteral administration or injection into or around the tumor.

The range and ratio of the chemotherapeutic agent to the anti-cancer compound will depend on the type of chemotherapeutic agent and the cancer being treated.

F. Dosage Delivery Forms

The anti-cancer compounds and chemotherapeutic agents are typically mixed with a pharmaceutically acceptable carrier. This carrier can be a solid or liquid and the type is generally chosen based on the type of administration being used. Liposomes may also be used to deliver the composition. The active agent can be coadministered in the form of a tablet or capsule, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms would also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described in the following references: 7 *Modern Pharmaceutics,* Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms 2nd Edition* (1976).

G. Method of Treatment

The method of treatment can be any suitable method which is effective in the treatment of the particular cancer type or tumor that is being treated. Treatment may be oral, rectal, topical, parenteral or intravenous administration or by injection into the tumor and the like. The method of applying an effective amount also varies depending on the tumor being treated. It is believed that parenteral treatment by intravenous, subcutaneous, or intramuscular application of the 1H-1,2,4-triazole compounds, formulated with an appropriate carrier, additional cancer inhibiting compound or compounds or diluent to facilitate application will be the preferred method of administering the compounds to warm blooded animals.

The method of treating viral infections may also be by oral, rectal, topical, parenteral or intravenous administration. A preferred method of treatment for viral infection is the administration of procodazole and propiconazole.

The 1H-1,2,4-triazole derivatives can also be administered with other fungicides such as benzimidazole derivatives, e.g., thiabendazole, benomyl, carbendazim; N-phosphonoglycines, e.g., glyphosate and herbicides such as N-chlorophenyl carbamates and N-chloro-thiocarbamates, e.g., chloroprofam.

They can also be used with griseofulvin.

Anti-Viral Evaluation with Human Influenza Virus

Female CD (mice Charles River Breeding Laboratories, Portage, Mich.) 5 to 7 weeks old of age at the time of receipt are used. Mice are approximately 6 to 9 weeks old and weigh approximately 20 to 28 grams at the time test initiation. All mice used in the study will not vary in age by more than 10 days. The mice are housed 6 per cage with bedding. The mice are fed rodent diet 5002 (PMI, St. Louis Mo.) adlibitum. Fresh water is supplied to the mice adlibitum.

Human influenza virus, strain AT2/Taiwan/1/64 is used to challenge the mice. The organism is stored at approximately −70° C. Prior to infectious challenge a vial of frozen stock is thawed and diluted to the appropriate concentration in buffered saline solution. The mice are anesthetized with Halothane and the virus challenge dose is administered intra-nasally in volume of 50 microliters.

Test articles are administered at the concentration and volume as provided below. On days 1 through 14, 10 mice per group receive the test articles by oral lavage. Saline control animals (10) receive a comparable volume of saline as compared to the test article-dosed mice. Test article dosing is accomplished at approximately 24 hour intervals. On day 0 approximately 4 hours after the second dosing of test articles or saline, all mice are challenged intra-nasally with an infective dose of virus calculated to produce approximately 90% lethality. Animals are observed daily for 21 days after infectious challenge for mortality or moribundity. Test animals will be observed twice after dosing on day 1, three times on day 0 and twice daily thereafter. Mice dying on test will be disposed of without necroscopy.

At 175 mg/kg dose of Propiconazole 40% of the mice survived compared to a saline control in which no mice survived. At 350 mg/kg dose 57% of the mice survived.

Anti-Viral Evaluation with Rhinovirus

In an in vitro screening for Rhinovirus, type A-1, cell line WI-38, propiconazole was effective at 32 µg/ml. The positive control was A-36683 of Abbot Company, (S,S)-1,2-bis (5-methoxy-2-benzimidazolyl)-1,2-ethanediol. A-36683 has a therapeutic index of 1000–3200. Propiconazole has a therapeutic index of 1–3. (See Schleicher et al, *Applied Microbiology,* 23, No. 1, 113–116 (1972).

In Vitro Human Tumor Colony Forming Units Test

Solid tumors removed by patients are minced into 2 to 5 mm fragments and immediately placed in McCoy's Medium SA plus 10% heat inactivated newborn calf serum plus 1% penicillin/streptomycin. Within 4 hours, these solid tumors are mechanically disassociated with scissors, forced through No. 100 stainless steel mesh, through 25 gauge needles, and then washed with McCoy's medium as described above. Ascitic, pleural, pericardial fluids and bone marrow are obtained by standard techniques. The fluid or marrow is placed in sterile containers containing 10 units of preservative free heparin per ml. of malignant fluid or marrow. After centrifugation at 150×g for 10 minutes, the cells are harvested and washed with McCoy's medium plus 10% heat inactivated calf serum. The viability of cell suspensions is determined on a hemocytometer with trypan blue.

Cells to be cloned are suspended in 0.3% agar in enriched CMRL1066 supplemented with 15% heat inactivated horse serum, penicillin (100 units/ml), streptomycin (2 mg/ml), glutamine (2 mM), insulin (3 units/ml), asparagine (0.6 mg/ml), and HEPES buffer (2 mM). For the continuous exposure test each compound is added to the above mixture. Cells are placed in 35 mm petri dishes in a top layer of agar over an underlayer of agar to prevent growth of fibroblasts. Three plates are prepared for each data point. The plates are placed in a 37° C. incubator, and are removed on day 14 for counting of the number of colonies in each plate. The number of colonies (defined as 50 cells) formed in the 3 compound treated plates is compared to the number of colonies formed in the 3 control plates, and the percent colonies surviving at the concentration of compound can be estimated. Three positive control plates are used to determine survival rate. Orthosodium vanadate at 200 µg/ml is used as the positive control. If there is <30% colonies in the positive control when compared to the untreated control, the test is evaluated.

At concentration of 0.5 and 5.0 µg/ml in a single dose experiment propiconazole was not effective (0/1) against tumors in this test. At concentration of 50.0 µg/ml in a continuous exposure experiment propiconazole was effective against colon, lung (non-small cell) melanoma and ovarian cancers. Over all 6 of 8 had ≦50% survival.

What is claimed is:

1. A pharmaceutical composition for treating cancers comprising a pharmaceutically acceptable carrier and a safe and effective amount of a chemotherapeutic agent and a safe and effective amount of a triazole or the formula:

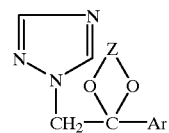

wherein Z is an alkylene selected from the group consisting of $CH_2-CH_2-$, $-CH_2-CH_2-CH_2-$, $-CH(CH_3)-CH$ (CH₃)— and —CH₂—CH(alkyl) wherein said alkyl has from 1 to about 10 carbon atoms; and Ar is a member selected from the group consisting of phenyl, substituted phenyl, thienyl, halothienyl, naphthyl and fluorenyl.

2. A pharmaceutical composition according to claim 1 comprising a pharmaceutically acceptable carrier and a safe and effective amount of a 1H-1,2,4-triazole selected from the group-consisting of:

1-[2-(2,4-dichlorophenyl)-1,3-dioxolan-2-ylmethyl]-1H-1,2,4-triazole;
1-[2-(2,4-dichlorophenyl)-4-methyl-1,3-dioxolan-2-ylmethyl]-1H-1,2,4-triazole,
1-[2-(2,4-dichlorophenyl)-4-ethyl-1,3-dioxolan-2-ylmethyl]-1H-1,2,4-triazole,
1-[2-(2,4-dichlorophenyl)-4-propyl-1,3-dioxolan-2-ylmethyl]-1H-1,2,4-triazole,
1-[2-(2,4-dichlorophenyl)-4-pentyl-1,3-dioxolan-2-ylmethyl]-1H-1,2,4-triazole, and the therapeutically active acid addition salts thereof.

3. A pharmaceutical composition according to claim 2 wherein said pharmaceutical acceptable acid addition salts are selected from the group consisting of chlorides, bromides, sulfates, nitrates, phosphates, sulfonates, formates, tartrates, maleates, malates, citrates, benzoates, salicylates, ascorbates and mixtures thereof.

4. A pharmaceutical composition according to claim 2 wherein said chemotherapeutic agent is selected from the group consisting of alkylating agents, DNA strand-breaking agents, intercalating topoisomerase II inhibitors, nonintercalating topoisomerase II inhibitors, DNA minor groove binders, Antimetabolites, Tubulin-binding Agents that when bound to tubulin prevent formation of microtubules, hormones, Asparaginase and hydroxyurea.

5. A pharmaceutical composition according to claim 4 wherein said chemotherapeutic agent is selected from the group consisting of Asparaginase, hydroxyurea, Cisplatin, Cyclophosphamide, Altretamine, Bleomycin, Dactinomycin, Doxorubicin, Etoposide, Teniposide, and Plicamycin.

6. A pharmaceutical composition according to claim 4 wherein said chemotherapeutic agent is selected from the group consisting of Methotrexate, Fluorouracil, Fluorodeoxyuridine, CB3717, Azacitidine, Cytarabine, Floxuridine, Mercaptopurine, 6-Thioguanine, Fludarabine, Pentostatin, Cyctrabine, and Fludarabine.

7. A method of treating cancer in warm blooded mammals comprising administering a safe and effective amount of a chemotherapeutic agent and a safe and effective amount of a 1H-1,2,4-triazole derivative of the formula:

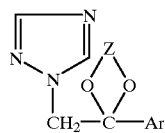

wherein Z is an alkylene selected from the group consisting of —CH₂—CH₂—,—CH₂—CH₂—CH₂—, —CH(CH₃)—CH(CH₃)— and —CH₂—CH(alkyl) wherein said alkyl has from 1 to about 10 carbon atoms; and Ar is a member selected from the group consisting of phenyl, substituted phenyl, thienyl, halothienyl, naphthyl and fluorenyl.

8. A method according to claim 7 wherein from about 2 mg/kg body weight to about 400 mg/kg of said 1H-1,2,4-triazole is administered and from 0.5 mg/kg body weight to about 40 mg/kg body weight of said chemotherapeutic agent is administered.

9. A method according to claim 8 wherein said 1H-1,2,4-triazole is administered orally or enterically, intravenously, peritoneally, parenterally or by injection into the tumor.

10. A method according to claim 7 wherein said 1H-1,2,4-triazole is administered in a solid form, liquid form or as a liposome.

11. A method according to claim 7 wherein said 1H-1,2,4-triazole is selected from the group consisting of:

1-[2-(2,4-dichlorophenyl)-1,3-dioxolan-2-ylmethyl]-1H-1,2,4-triazole;
1-[2-(2,4-dichlorophenyl)-4-methyl-1,3-dioxolan-2-ylmethyl]-1H-1,2,4-triazole,
1-[2-(2,4-dichlorophenyl)-4-ethyl-1,3-dioxolan-2-ylmethyl]-1H-1,2,4-triazole,
1-[2-(2,4-dichlorophenyl)-4-propyl-1,3-dioxolan-2-ylmethyl]-1H-1,2,4-triazole,
1-[2-(2,4-dichlorophenyl)-4-pentyl-1,3-dioxolan-2-ylmethyl]-1H-1,2,4-triazole, and the therapeutically active acid addition salts thereof.

12. A method according to claim 11 wherein said pharmaceutically acceptable acid addition salts are selected from the group consisting of chlorides, bromides, sulfates, nitrates, phosphates, sulfonates, formates, tartrates, maleates, malates, citrates, benzoates, salicylates, ascorbates and mixtures thereof.

13. A method according to claim 7 wherein said chemotherapeutic agent is selected from the group consisting of alkylating agents, DNA strand-breaking agents, intercalating topoisomerase II inhibitors, nonintercalating topoisomerase II inhibitors, DNA minor groove binders, Antimetabolites, Tubulin-binding Agents that when bound to tubulin prevent formation of microtubules, hormones, Asparaginase and hydroxyurea.

14. A method according to claim 13 wherein said chemotherapeutic agent is selected from the group consisting of Asparaginase, hydroxyurea, Cisplatin, Cyclophosphamide, Altretamine, Bleomycin, Dactinomycin, Doxorubicin, Etoposide, Teniposide, and Plicamycin.

15. A method according to claim 13 wherein said chemotherapeutic agent is selected from the group consisting of Methotrexate, Fluorouracil, Fluorodeoxyuridine, CB3717, Azacitidine, Cytarabine, Floxuridine, Mercaptopurine, 6-Thioguanine, Fludarabine, Pentostatin, Cyctrabine, and Fludarabine.

16. A method of treating viral infections in warm blooded mammals comprising administering a safe and effective amount of a 1H-1,2,4-triazole derivative of the formula:

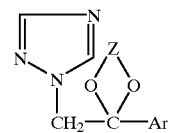

wherein Z is an alkylene selected from the group consisting of CH₂—CH₂—,—CH₂—CH₂—CH₂—, —CH(CH₃)—CH(CH₃)— and —CH₂—CH(alkyl) wherein said alkyl has from 1 to about 10 carbon atoms; and Ar is a member selected from the group consisting of phenyl, substituted phenyl, thienyl, halothienyl, naphthyl and fluorenyl and a potentiator.

17. A method according to claim 16 wherein said potentiator is procodazole.

18. The method of claim 7 wherein the cancer is colon cancer.

19. The method of claim 7 wherein the cancer is non small cell lung cancer.

20. The method of claim 7 wherein the cancer is melanoma cancer.

21. The method of claim 7 wherein the cancer is ovarian cancer.

22. The method of claim 16 wherein the viral infection is an influenza virus infection.

23. The method of claim 16 wherein the viral infection is a rhinovirus infection.

* * * * *

UNITED STATES PATENT AND TRADEMARK OFFICE
CERTIFICATE OF CORRECTION

PATENT NO. : 6,110,953
DATED : August 29, 2000
INVENTOR(S) : James Berger Camden It is certified that error appears in the above-identified patent and that said Letters Patent is hereby corrected as shown below:

Title page,
Please correct Item [62], Division of application serial no. 08/674,182 filed on Jul. 16, 1996, which is a continuation-in-part application of serial no. 08/473,819 filed Jun. 7, 1995, now Pat. No. 5,770,616.

Item [60], Provisional application No. 60/001,838 filed on Aug. 3, 1995.

Column 1,
Line 5, after "Jul. 16, 1996" insert -- which claims benefit of 60/001,838 filed Aug. 3, 1995 and is a continuation-in-part application of serial no. 08/473,819 filed Jun. 7, 1995, now Pat. No. 5,770,616 --.

Signed and Sealed this

Eighth Day of January, 2002

*Attest:*

JAMES E. ROGAN
*Attesting Officer*     *Director of the United States Patent and Trademark Office*